United States Patent
Kim et al.

(10) Patent No.: US 10,010,719 B2
(45) Date of Patent: Jul. 3, 2018

(54) TRIPLE ENDORECTAL BALLOONING SYSTEM FOR PROSTATE CANCER RADIOTHERAPY

(71) Applicant: Yonsei University Wonju Industry-Academic Cooperation Foundation, Wonju-si (KR)

(72) Inventors: Won-Ky Kim, Wonju-si (KR); Sei-Hwan You, Wonju-si (KR)

(73) Assignee: Yonsei University Wonju Industry-Academic Cooperation Foundation, Wonju-si (KR)

( * ) Notice: Subject to any disclaimer, the term of this patent is extended or adjusted under 35 U.S.C. 154(b) by 155 days.

(21) Appl. No.: 15/032,860

(22) PCT Filed: Apr. 14, 2014

(86) PCT No.: PCT/KR2014/003179
§ 371 (c)(1),
(2) Date: Apr. 28, 2016

(87) PCT Pub. No.: WO2015/064861
PCT Pub. Date: May 7, 2015

(65) Prior Publication Data
US 2016/0263398 A1 Sep. 15, 2016

(30) Foreign Application Priority Data
Oct. 31, 2013 (KR) ........................ 10-2013-0130719

(51) Int. Cl.
*A61N 5/00* (2006.01)
*A61N 5/10* (2006.01)
*A61M 25/10* (2013.01)

(52) U.S. Cl.
CPC ............ *A61N 5/10* (2013.01); *A61M 25/1011* (2013.01); *A61N 2005/1094* (2013.01); *A61N 2005/1096* (2013.01); *A61N 2005/1097* (2013.01)

(58) Field of Classification Search
CPC ......... A61N 5/10; A61M 25/00; A61M 25/10; A61M 25/1011
(Continued)

(56) References Cited

FOREIGN PATENT DOCUMENTS

| EP | 0 261 831 B1 | 6/1992 |
|---|---|---|
| JP | 5-51356 U | 7/1993 |

(Continued)

OTHER PUBLICATIONS

International Search Report and Written Opinion (with English Translation) dated May 30, 2014 corresponding to International Application No. PCT/KR2014/003179; 18 Pages.

(Continued)

*Primary Examiner* — John Lacyk
(74) *Attorney, Agent, or Firm* — Daly, Crowley, Mofford & Durkee, LLP

(57) ABSTRACT

A triple endorectal ballooning (TERB) system for prostate cancer radiotherapy may include a first balloon unit, a second balloon unit, a third balloon unit, a central passageway and a cover. The first balloon unit may include a first balloon and a first passageway connected to the first balloon. The second balloon unit may include a second balloon and a second passageway connected to the second balloon. The third balloon unit may include a third balloon and a third passageway connected to the third balloon. The central passageway may be arranged between the first to third balloon units to excrete a bowel gas. The cover may be (Continued)

configured to cover the first to third passageways and the central passageway and to support the first to third balloon units.

8 Claims, 5 Drawing Sheets

(58) Field of Classification Search
USPC .......................................................... 600/1–8
See application file for complete search history.

(56) References Cited

FOREIGN PATENT DOCUMENTS

| JP | 2006-500103 A | 1/2006 |
|---|---|---|
| KR | 2013-0009445 A | 1/2013 |
| WO | WO 2005/007000 A1 | 1/2005 |

OTHER PUBLICATIONS

International Preliminary Report dated May 3, 2016 corresponding to International Application No. PCT/KR2014/003179; 8 Pages.

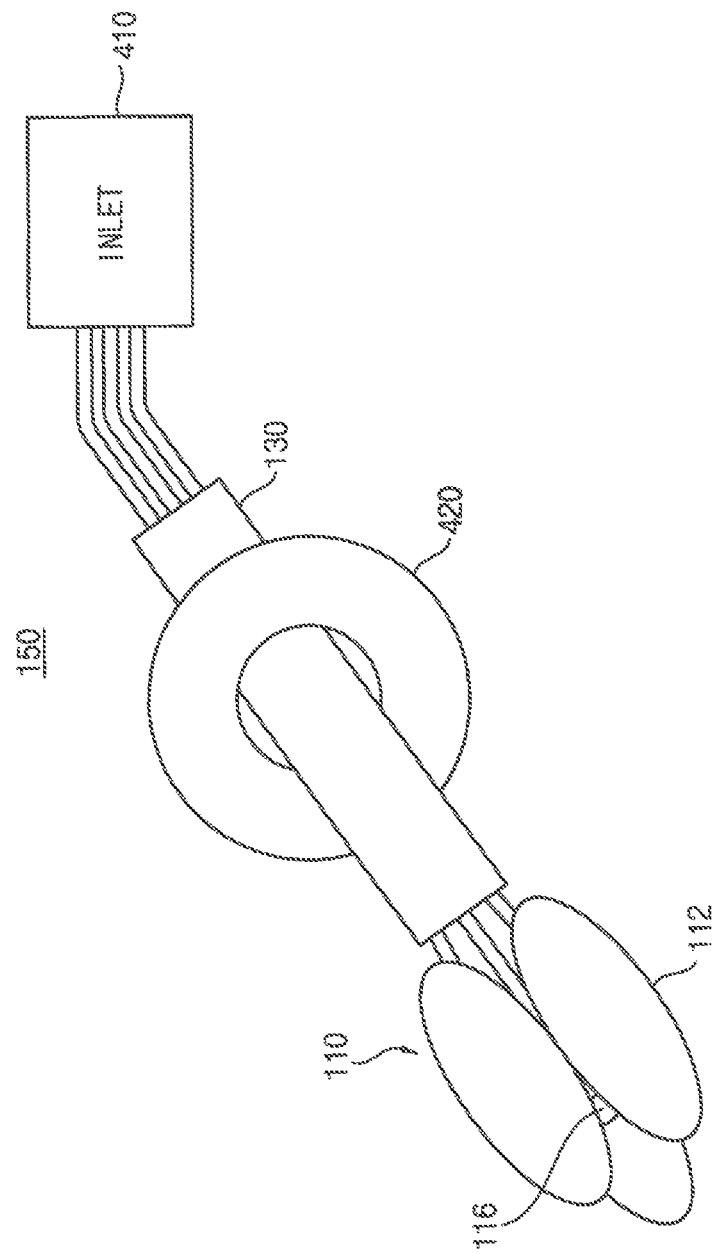

TRIPLE ENDORECTAL BALLOONING SYSTEM FOR PROSTATE CANCER RADIOTHERAPY

CROSS REFERENCE TO RELATED APPLICATIONS

This application is a U.S. National Stage of PCT application PCT/KR2014/003179 filed in the Korean language on Apr. 14, 2014, entitled "TRIPLE ENDORECTAL BALLOONING SYSTEM FOR PROSTATE CANCER RADIOTHERAPY," which claims priority to Korean application 10-2013-0130719, flied on Oct. 31, 2013, which applications are each hereby incorporated herein by reference in their entireties.

BACKGROUND

1. Field

Example embodiments relate to a triple endorectal ballooning (TERB) system in the rectum. More particularly, example embodiments relate to a TERB system in the rectum for prostate cancer radiotherapy.

2. Description of the Related Art

External beam radiotherapy as a typical treatment for prostate cancer has non-invasive characteristics and low side effects. A highly accurate radiotherapy technique such as intensity modulation has amplified this advantage. However, a radiation toxicity to the rectum or anus may be increased according to dose escalation scheme. Recently, rectal ballooning method is preferred in order to decrease the recto-anal radiation toxicity.

Previous ballooning systems being used for prostate cancer treatment may not be applied to patients who have different rectal anatomies and functions. Further, it is difficult to standardize the ballooning system due to different manufacture and authorization system. In many cases, the balloon cannot be accurately located in the rectum due to feces and bowel gas. Further, balloon insertion is dependent upon subjective experiences and feelings of medical operators without standardized protocol. Thus, the balloon cannot be localized at the optimal position reproductively in the rectum. This unstable balloon localization may cause repeated and consumptive results for the patient and medical personnels.

One of the most significant factors of unstable balloon localization is unpredictable bowel gas status.

The entrant single endorectal ballooning system generally have only one central passage way, which makes bowel gas excretion less effective. Because of the cost problem, the balloon may not be used disposably. In this case, the gas excretion can be more difficult due to gas passageway obstruction resulted from hygiene-aimed condom use.

When the endorectal balloon is inflated with air, the actual rectal wall dose may be decreased compared with planned dose due to the specific gravity difference between the air and the rectal wall. This means the possibility of improper prostate cancer treatment despite effective recto-anal wall protection. In contrast, when the injected medium is composed of water, the posterior prostatic dose can be relevant at the expense of rectal wall toxicity increase. This is also the limitation, of the conventional single endorectal ballooning system.

SUMMARY

Example embodiments may exhibit the triple endorectal ballooning (TERB) system which may be capable of excreting bowel gas effectively and localizing the balloon stably in prostate cancer radiotherapy.

According to example embodiments, TERB system may include three balloon units, a central passageway, and a cover. The first balloon unit includes a balloon and a passageway connected to the balloon. The second balloon unit includes a balloon and a passageway connected to the balloon. The third balloon unit includes a third balloon and a third passageway connected to the third balloon. The central passageway may be arranged among the three balloon units to excrete the bowel gas. The cover may be configured to cover the three passageways and the central passageway supporting each balloon unit.

In example embodiments, the three balloons may be expanded by injecting agents to form two types of spaces. The first type of space may be formed between the central passageway and three balloons. The second type of spaces may be built between the three balloons and the rectal wall. Each space may be used for excreting bowel gas.

In example embodiments, the first balloon adjacent to anterior rectal wall may be expanded. The second and third balloons may be configured to support the first balloon upwardly, which makes stable the prostatic localization.

In example embodiments, TERB system may further include an inlet connected to the first to third passageways through which the air or liquid may be injected into each passageway.

In example embodiments, the three balloons may be sequentially or simultaneously expanded by injecting the media into the three corresponding passageways through the inlet.

In example embodiment, the injection into the first balloon may be water-mediated. The injection into the second and third balloons may be mediated by air.

In example embodiments, the first to third balloons may be sequentially or simultaneously contracted by discharging the injection agents from the first to third passageways through the inlet.

In example embodiments, the cover and the first to third passageways may be made of flexible materials.

According to example embodiments, the TERB system may include four passageways through which bowel gas may be excreted. Even when the balloons may be covered with rubber sheath, the TERB system may ensure at least three passageways so that the bowel gas may be excreted effectively.

The water or air-based agents may be injected into the first to third balloons sequentially or simultaneously through the individual inlets connected to each balloon. The second and third balloons may be positioned under the first balloon which may be beneath the prostate gland so that the expanded second and third balloons may support the expanded first balloon and the prostate gland.

When the water may be injected into the first balloon beneath, the prostate and the air may be injected into the second and third balloons, the radiation dose to the rectal wall may be decreased without compromising the posterior prostatic dose.

The first to third balloons may be contracted sequentially or simultaneously through the individual inlets connected to each passageway so that the balloons may be readily taken out from the rectum after performing the procedure.

The TERB system may include the innocuous flexible materials so feat prostate cancer patients may be treated more comfortably.

BRIEF DESCRIPTION OF THE DRAWINGS

Example embodiments will be understood more clearly from the following detailed description takes is conjunction with the accompanying drawings, FIGS. 1 to 5 represent non-limiting, example embodiments as described herein.

FIG. 1 is a cross-sectional view illustrating the conventional single endorectal ballooning system in the rectum;

FIG. 2 is a cross-sectional view illustrating the triple endorectal ballooning (TERB) system in accordance with example embodiments;

FIG. 4 is a perspective view illustrating the TERB system in FIG. 2; and

FIG. 5 is a cross-sectional view illustrating the TERB system connected to an inlet in FIG. 2.

DETAILED DESCRIPTION OF THE EMBODIMENTS

Figure 1:
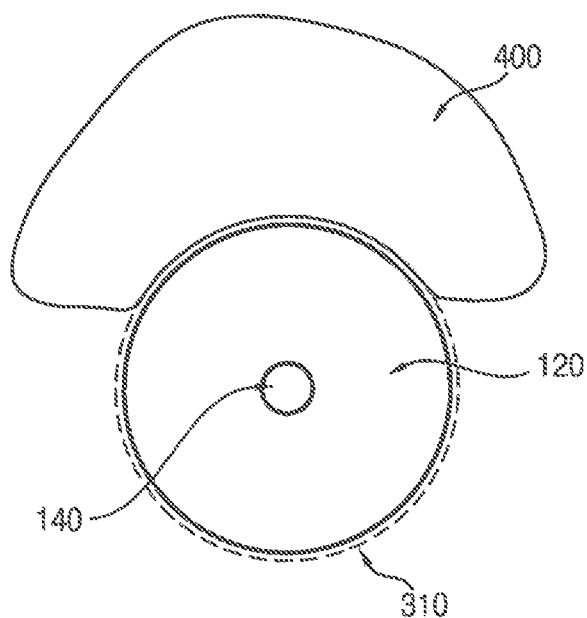

Various example embodiments will be described more fully hereinafter with reference to the accompanying drawings, in which some example embodiments are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element, or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although, the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular drapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

FIG. 1 is a cross-sectional view illustrating the conventional single endorectal ballooning system.

Referring to FIG. 1, a conventional balloon 120 may be positioned in a rectum 310 beneath a prostate 400. When a gas may be injected into the balloon 120, the balloon 120 may be expanded. A central passageway 140 through, which a bowel gas may be excreted may be formed at a central portion of the balloon 120. The expanded balloon 120 may expand an upper portion of the rectum 310. The expanded upper portion of the rectum 310 may make contact with a lower portion of the prostate 400.

FIG. 2 is a cross-sectional view illustrating the triple endorectal ballooning (TERB) system in accordance with example embodiments.

Referring to FIG. 2, the TERB system 150 of this example embodiment may include a first balloon unit, a second balloon unit, a third balloon unit, an inlet 410, a central passageway 116 and a cover 130.

The first balloon unit may include a first balloon and a first passageway. The second balloon unit may include a second balloon and a second passageway. The third balloon unit may include a third balloon and a third passageway.

The first to third balloons may have an elliptical shape to be readily inserted into the rectum. In order to prevent damages of the viscera when the first to third balloons may be inserted into the viscera, a gel lubricant or a lubricating oil may be coated on the first to third balloons.

When the first to third balloons may be covered with a condom, the gel lubricant or the lubricating oil may be coated on the condom to prevent damages of the viscera during the TERB system 150 may be inserted into the rectum.

An injection agent such as a gas or a liquid may be injected into the first to third balloons through the inlet 410 to expand the first to third balloons. Each of the first to third passageways may have a first end connected to each of the first to third balloons, and a second end opposite to the first end connected to the inlet 410. Thus, the first to third balloons may be connected to the first to third passageways, respectively, to form the fast to third balloon units. The first to third balloon units may have structures in fluidic communication with the first to third passageways connected to the inlet 410. In order to take out the TERB system 150 from, the rectum after performing a treatment, the injection agent may be discharged through the inlet 400. Further, the inlet 410 may have a function as to stably localize the first to third balloons and adjust sizes of the first to third balloons as well as take out the TERB system 150 from the rectum. In order to contract the first to third balloons along shapes of the first to third balloons inserted into the viscera when the injection agent may be discharged through the inlet 410, the first to third passageways connected to the first to third balloons may function as supports. A pump, a syringe, a mini air injector, etc., may be used for the inlet 410.

When the TERB system 150 may be inserted into the rectum, the injection agent may be discharged through, the central passageway 116. Because the central passageway 116 may only function as to discharge the injection agent from the TERB system 150, the central passageway 116 may not be connected with the inlet 410.

The cover 130 may include the central passageway 116 and the first to third passageways. The cover 130 may include an innocuous flexible material. The cover 130 may have rounded corners. The cover 130 may be configured to cover the first to third passageways and the central passageway 116 to stably support the TERB system 150 inserted into the rectum.

In order to prevent damages of the viscera when, the first to third balloons may be deeply inserted into the rectum, a stopper 420 may be detachably installed on the cover 130. The stopper 420 may be slidable on the cover 130 in accordance with a depth of the treatment in the rectum. The stopper 420 may include an innocuous flexible material.

In example embodiments, the gas may be injected into the TERB system 150. Alternatively, the liquid or the liquid and the gas may be injected into the TERB system 150. Further, the TERB system ISO may be used for treating other cancers such as a uterine cervical cancer. Alternatively, the TERB system 150 may include two balloons or at least four balloons in accordance with, treatment portions or treatment method in the viscera.

Figure 3A:
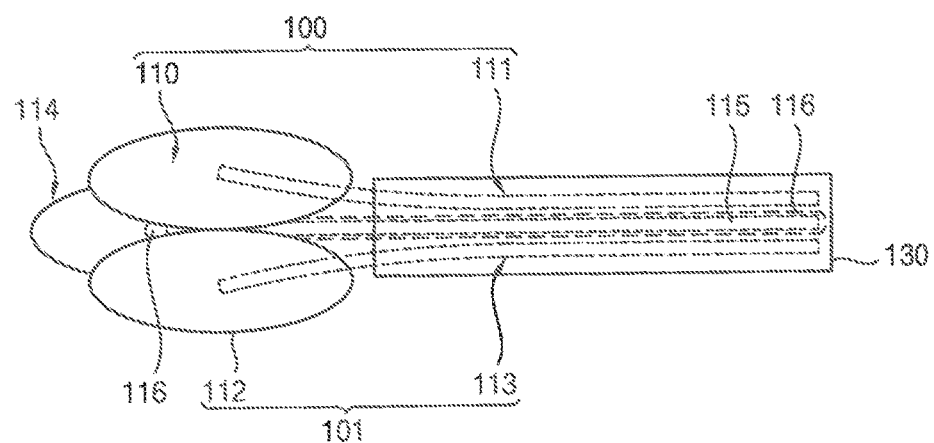
FIGS. 3A and 3B are perspective views illustrating the TERB system in FIG. 2.
Figure 3B:
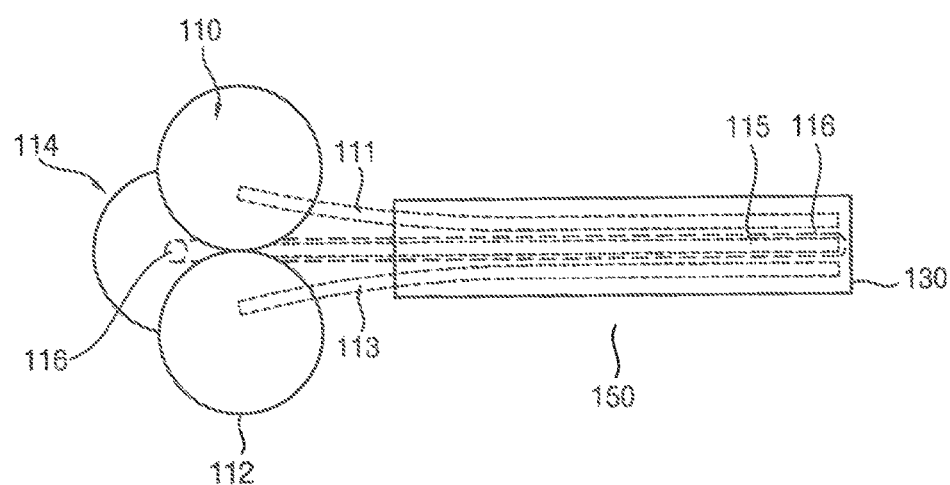
Figure 4:
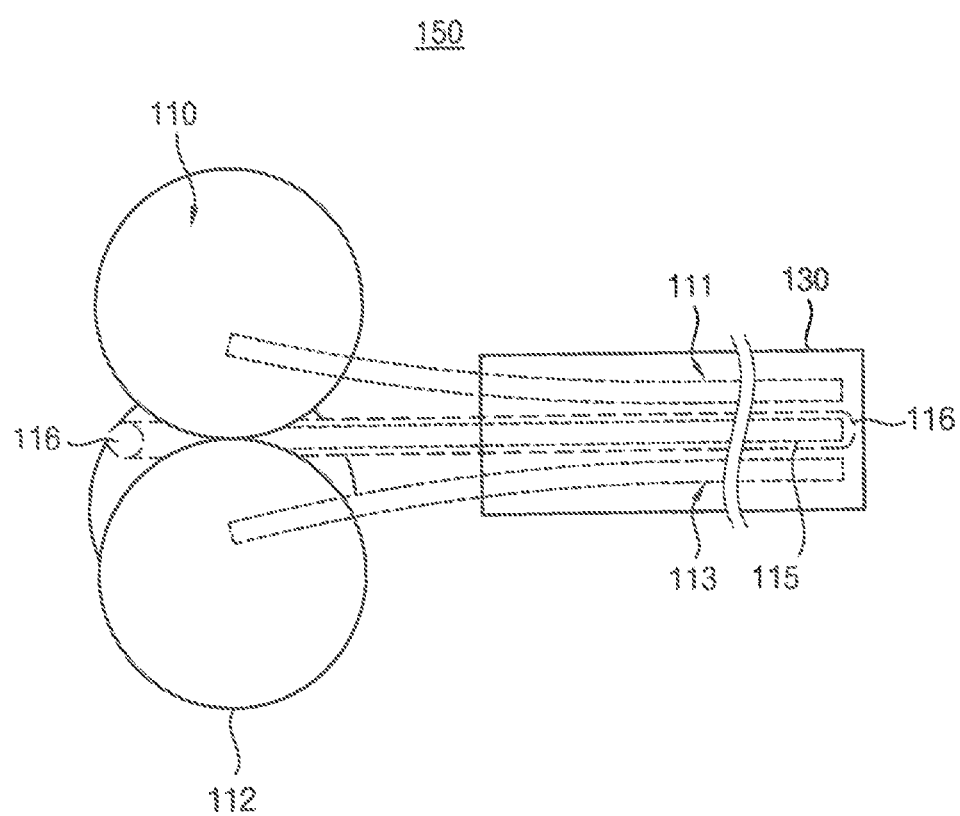

FIGS. 3A and 3B are perspective views illustrating the TERB system, in FIG. 2, and FIG. 4 is a perspective view illustrating the TERB system in FIG. 2.

Referring to FIGS. 3A, 3B and 4, the first to third balloons 110, 112 and 114 may be connected to the first to third passageways, respectively. The central passageway 116 may have a first end in the first to third balloons, and a second end opposite to the first end and connected to the inlet 400. The cover 130 may include the first to third passageways and fee central passageway 116.

The first to third balloons 110, 112 and 114 may be connected with the first to third passageways, respectively. After inserting the TERB system 150 into the rectum 310, the gas may be injected into the first to third balloons 110, 112 and 114 so that the first to third balloons 110, 112 and 114 may be expanded simultaneously with each other. Alternatively, the first to third balloons 110, 112 and 114 may be sequentially expanded. For example, after the second and third balloons 112 and 114 may be expanded, the first balloon 110 may be expanded so as to adjust a position of the expanded first balloon 110. This expansion sequence may function as to stably localize the first balloon 110 in the rectum 310 beneath the prostate 400. Alternatively, after the first balloon 110 may be expanded, the second and third balloons 112 and 114 may be expanded so as to adjust a position of the expanded first balloon 110. The first to third passageways may have ends terminated at inner feces of the first to third balloons 110, 112 and 114. Portions of the first to third passageways in the first to third balloons 110, 112 and 114 may have holes through which the injection agent may be injected.

The first to third balloons 110, 112 and 114 outside the viscera may not include the air. The first to third balloons 110, 112 and 114 may be arranged without tangles. When the TERB system 150 may be inserted into the rectum, the first to third passageways and the cover 130 may function as to support the first to third balloons 110, 112 and 114 to prevent the first to third balloons 110, 112 and 114 from being tangled.

Figure 5:
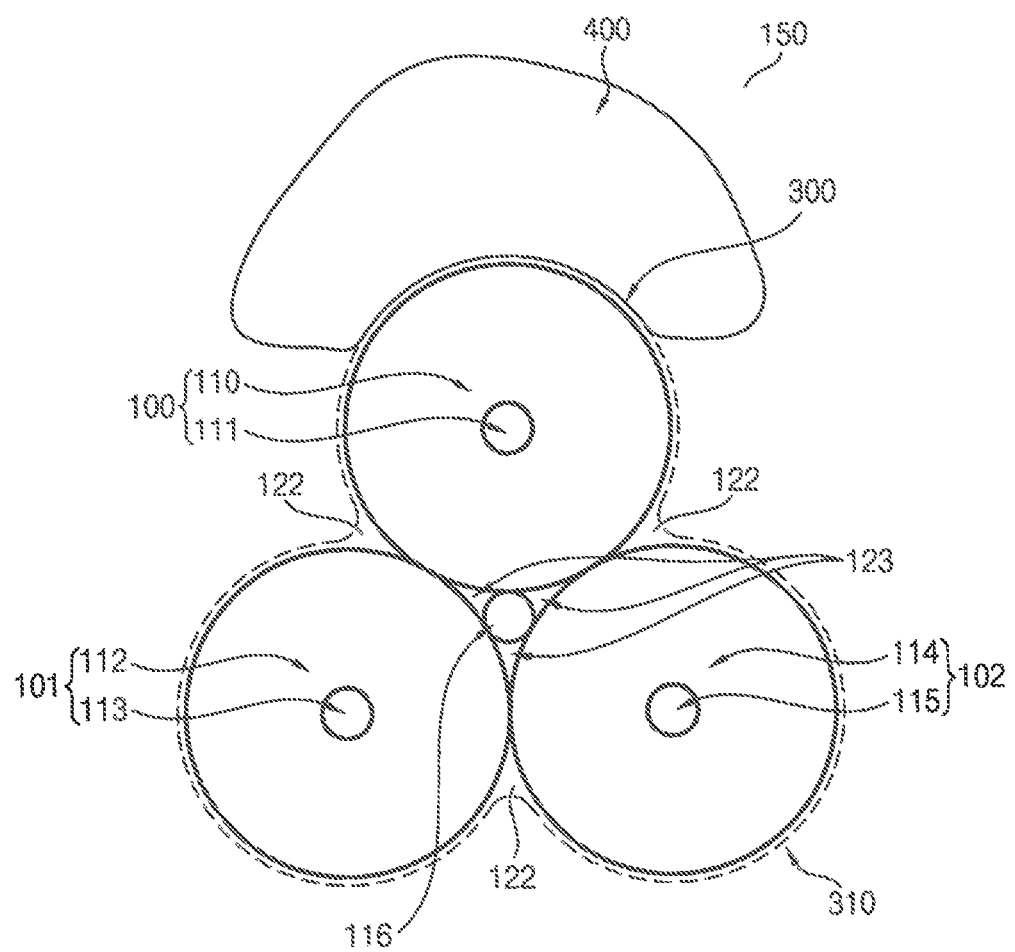

FIG. 5 is a side view illustrating the TERB system connected to an inlet in FIG. 2.

Referring to FIG. 5, the TERB system 150 may be positioned in the rectum 310. The expanded first to third balloons 110, 112 and 114 may compress as upper portion of the rectum 310 to support the prostate 400. The first to third passageways 111, 113 and 115 may be positioned at the central portions of the first to third balloons 110, 112 and 114. The infection agent may be supplied to the first to third balloons 110, 112 and 114 through the first to third passageways 111, 113 and 115. The first balloon 110 may make contact with the wall of the rectum 310 to upwardly support the prostate 400 making contact with the wall of the rectum 310. When the radiation may be irradiated to the prostate 400 supported by the rectum 310 and the TERB system 150, rectal toxicity may be remarkably reduced because the first balloon 110 may have a radius shorter than that of the conventional balloon 120.

When the water may be injected into the conventional balloon 120 closely adjacent to the wall of the rectum 310, the radiation may be distributed sufficiently and stably on the prostate 400 because the water may have a specific gravity substantially similar to that of the viscera. However, the rectum 310 may be damaged due to increasing the dosage of the radiation. When the sir may be injected into the conventional balloon 120 closely adjacent to the wall of the rectum 310, the damages of the rectum 310 may be decreased due to the characteristic of the radiation with respect to the specific gravity difference between the air and the viscera. However, because the dosage of the radiation may be decreased, the prostate cancer may not be effectively treated.

Therefore, as shown in FIG. 5, the water may be injected into the first balloon 110 adjacent to the rectum 310 and the air may be injected into the second and third balloons 112 and 114 to stably irradiate the radiation to the prostate 400 and reduce the damages of the rectum 310. When the liquid may be injected into the first balloon 110 and the gas may be injected into the second and third balloons 112 and 114, the water having the specific gravity higher than that of the air may be injected into the first balloon 110 after expanding the second and third balloons 112 and 114 to stably localize the first balloon 110 in the rectum 310. When the TERB system 150 may be used for the uterine cervical cancer, other kinds of the liquid and the gas may be used in the TERB system 150. The first balloon 110 into which the liquid may be injected may include a material suitable for the specific gravity of the kinds of the liquid. Thus, various kinds of the liquid and the gas may be used in the TERB system 150 in accordance with the treatment portions and the treatment procedures.

When the first to third balloons 110, 112 and 114 may be inserted into the rectum, the gas and the liquid inserted through the inlet 410 may expand the first to third balloons 110, 112, 114. In order to discharge the bowel gas from the rectum 310, second spaces 123 may be formed between the first to third balloons 110, 112 and 114 and first spaces 122 may be formed between the first to third balloons 110, 112 and 114 and the rectum 310. The expanded first to third balloons 110, 112 and 114 may have a high resilience. When the condom may be used for the TERB system 150, the at least three first and second spaces 122 and 123 formed, by expanding the first to third balloons 110, 112 and 114 may function as to effectively discharge the bowel gas. Thus, the first to third balloons 110, 112 and 114 may be stably localized in the rectum 310 so that the eonomy of time and expenses may be improved because the repetitive computed tomography may not be required. An outer protector such as the condom may be fixed to the first to third balloons 110, 112 and 114 using a fixing unit so that the TERB system 150 may be repeatedly used to reduce treatment expenses. The first to third balloons 110, 112 and 114 may be detached so that the TERB system 150 may have eco-effects.

In order to readily take out the first to third balloons 110, 112 and 114 from the rectum, the innocuous lubricating oil or the gel type lubricant may be coated on the condom covering the first to third balloons 110, 112 and 114.

According to example embodiments, the TERB system may include the four passageways through which the bowel gas may be excreted to effectively excrete the bowel gas. When the balloons may be covered with a condom, the TERB system may include the at least two passageways so that the bowel gas may be effectively excreted.

The injection agent may be sequentially or simultaneously injected into the first to third balloons through the inlet individually connected to the first to third balloons so that the TERB system may be applied to various medical procedures. The second and third balloons may be positioned under the first balloon beneath the prostate so that the expanded second and third balloons may be previously positioned in the rectum to firmly support the expanded first balloon and the prostate.

When the water may be injected into the first balloon beneath the prostate and the air may be injected into the second and third balloons, a dosage of a radiation irradiated to the prostate may be stably maintained decreasing damages of a rectal wall.

The first to third balloons may be sequentially or simultaneously contracted by the inlet individually connected to the first to third passageways so that the balloons may be readily taken out from, tire rectum after performing the procedure.

The TERB system may include the innocuous flexible materials so that the prostate cancer patients may be stably treated without inconvenience.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present invention. Accordingly, all such modifications are intended to be included within fee scope of the present invention as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A triple endorectal ballooning (TERB) system for prostate cancer radiotherapy, the TERB system comprising:
   a first balloon unit including a first balloon and a first passageway connected to the first balloon;
   a second balloon unit including a second balloon and a second passageway connected to the second balloon;
   a third balloon unit including a third balloon and a third passageway connected to the third balloon;
   a central passageway arranged between the first to third balloon units to discharge a bowel gas from a viscera;
   a cover configured to cover the first to third passageways and the central passageway and to support the first to third balloon units and;
   a stopper detachably installed on the cover to prevent damages of the viscera by the first to third balloons.

2. The TERB system of claim 1, wherein the first to third balloons are expanded by injecting an injection agent into the first to third balloons to form first spaces between the first to third balloons and the central passageway, and second spaces between the first to third balloons and the rectal wall, and the bowel gas is discharged through the first and second spaces.

3. The TERB system of claim 1, wherein the first balloon is expanded in the rectum to make contact with the prostate gland, and the second and third balloons are configured to upwardly support the first balloon.

4. The TERB system of claim 1, further comprising an inlet connected to the first to third passageways, an injection agent injected into the first to the third balloons through the inlet.

5. The TERB system of claim 4, wherein the injection agent is injected into the first to third balloons through the inlet to sequentially or simultaneously expand the first to third balloons.

6. The TERB system of claim 4, wherein the first balloon is expanded by injecting a water into the first balloon through the inlet, and the second and third balloons are expanded by injecting a gas into the second and third balloons through the inlet.

7. The TERB system of claim 4, wherein the first to third balloons are sequentially or simultaneously contracted by discharging the injection agent from the first to third balloons through the inlet.

8. The TERB system of claim 1, wherein the cover and the first to third passageways comprise a flexible material.

* * * * *